United States Patent [19]

Peyman

[11] Patent Number: 4,617,023
[45] Date of Patent: Oct. 14, 1986

[54] INTRAOCULAR LENSES WITH OPENABLE HAPTIC LOOPS

[76] Inventor: Gholam A. Peyman, 535 N. Michigan Ave., Apt. 3001, Chicago, Ill. 60611

[21] Appl. No.: 490,858

[22] Filed: May 2, 1983

[51] Int. Cl.⁴ .............................................. A61F 2/16
[52] U.S. Cl. ...................................................... 623/6
[58] Field of Search ................................ 3/13, 1; 623/6

[56] References Cited

U.S. PATENT DOCUMENTS

| | | | |
|---|---|---|---|
| 4,073,014 | 2/1978 | Poler | 3/13 |
| 4,174,543 | 11/1979 | Kelman | 3/13 |
| 4,249,271 | 2/1981 | Poler | 3/13 |
| 4,257,294 | 7/1985 | Heslin | 623/6 |
| 4,280,232 | 7/1981 | Hummel | 3/13 |
| 4,403,354 | 9/1983 | Rainin | 3/13 |

OTHER PUBLICATIONS

Iolab advertisement (2 pages/price list effective date Jan. 1982), Model 103 R (Three-Point Capsular/Sulcus Posterior Chamber Lens).
Iolab Intraocular Lens catalog, Model 103 R Lens, 1982.
Barraquer, Joaquin, "Nuevos Modelos de Lentes Plásticas de Cámara Anterior," *Anales del Instituto Barraquer*, Sep. 1961, pp. 345–352.
"Implant Techniques," *IOL & Ocular Surgery News*, Jan. 15, 1983, p. 8.
Advertisements, *Opthalmology Times*, Nov. 1, 1982, pp. 4, 69, 83 and 85.
Advertisements, *Opthalmology Times*, Nov. 15, 1982, pp. 5, 21, 43 and inside back cover.

*Primary Examiner*—Ronald L. Frinks
*Attorney, Agent, or Firm*—Thomas A. Kmiotek

[57] ABSTRACT

Intraocular lenses are disclosed which have haptic loops or feet generally forming a closed or locked structure. The haptic loops are unlocked or sprung open once an intraocular lens is implanted in an eye thereby seating the lens in the eye. The intraocular lenses can be implanted in either the anterior chamber or posterior segment.

2 Claims, 15 Drawing Figures

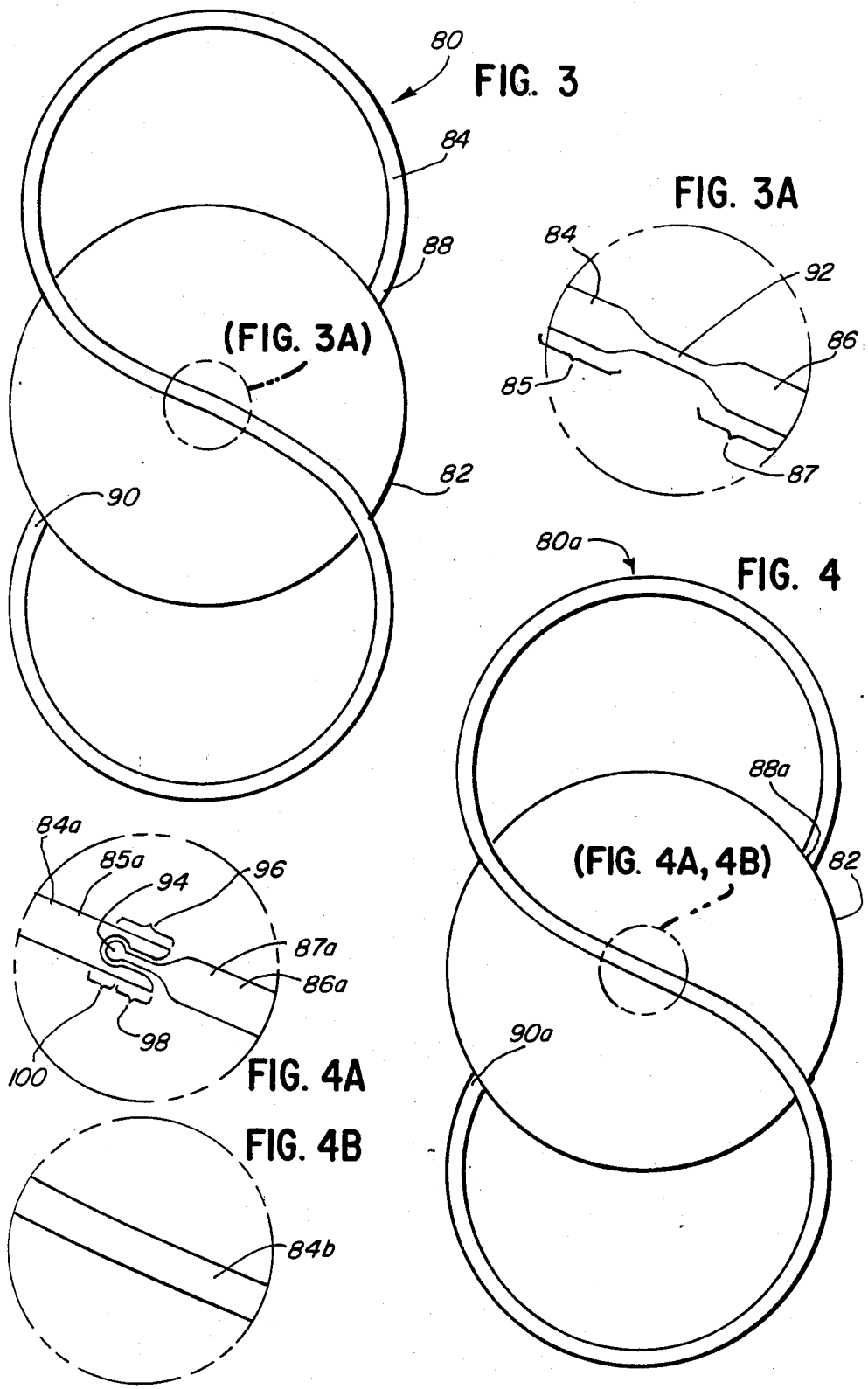

INTRAOCULAR LENSES WITH OPENABLE HAPTIC LOOPS

FIELD OF THE INVENTION

Intraocular lenses for implanting inside aphakic eyes are the general province of this invention. This invention specifically relates to intraocular lenses whose haptic loops or feet form a closed or locked structure which easily can be opened or unlocked once implanted in the eye. The intraocular lens of this invention can be implanted in either the anterior chamber or posterior segment.

BACKGROUND OF THE INVENTION

Currently, cataract extraction is the most common ophthalmic surgical procedure performed in the United States. Approximately 400,000 lenses are removed every year. These lenses, however, must be replaced with a prosthetic optical device before useful vision can be restored to the operated eye. With the lens removed, light rays are no longer focused on the retina and vision is very poor without corrective glasses, contact lenses or an intraocular lens.

Corrective eye glasses have been the classic and most common method of correcting aphakia. Corrective glasses, however, being located in front of the normal position of the human lens, can produce magnification and distort the shape of viewed objects. Contact lenses cause less magnification and distortion, but very old and very young patients frequently find handling and wearing these small lenses difficult. With implanted intraocular lenses, there is little or no magnification or distortion and there is no need to remove the lens from the eye or otherwise handle the lens. Generally, the lenses provide good visual acuity at all times, even at night.

Intraocular lenses have definite advantages in terms of vision and convenience over the other methods of aphakic correction. While intraocular lenses have definite advantages over corrective glasses and contact lenses, intraocular lenses have specific disadvantages.

Intraocular lens implantation surgery is more traumatic than simple cataract extraction alone. The additional handling of the cornea and manipulation inside the anterior chamber during lens implantation add to the amount of trauma to the eye. There also are certain surgical dogma that must be adhered to. It is a cardinal rule in any surgery that the surgeon have good exposure. In implant surgery, however, the surgeon must have excellent exposure. Extreme care must be exercised to limit trauma to the cornea, structures of the anterior chamber, and other structures.

A large number of different types and styles of intraocular lenses has been developed. Major classes of lenses can be distinguished based on the method of fixation in the eye. Anterior chamber lenses lie entirely in front of the iris. Iris-supported lenses rely on the structural integrity of the iris to stabilize and support the lens within the eye. Capsule-fixated lenses are inserted into a planned extracapsular cataract extraction space between the anterior and posterior leaves of the lens capsule.

Anterior chamber lenses rely on haptics, also called feet or loops, propped against the scleral spur in the chamber angle to support and fix the lens in the eye. Lenses must be carefully designed with thin feet or haptics to prevent the feet from touching the corneal endothelium.

Iris-supported lenses, on the other hand, have an arrangement of struts, or loops, some anterior and others posterior to the iris. These struts or loops function like a clip. Other iris type supported lenses require the iris to be interwoven about alternating feet, and some iris-supported lenses have small haptics with holes therein for direct suturing to the iris.

With capsule-fixated lenses, a planned extracapsular cataract extraction is performed. The haptics of the lens are then inserted into the space between the anterior and posterior leaves of the capsule. This is referred to as the "in-the-back" technique. The haptic loops, however, often are positioned in the ciliary body sulcus between the ciliary body and the iris root. If performed properly, the capsule and any residual lens cortex adhere firmly to the lens, fixing it securely in place. Good capsular fixation is much more stable than iris fixation, and movement of the implant in the eye is reduced.

Common to all lens classes, particularly anterior chamber lenses and capsule-fixated lenses, is trauma associated with implanting the lens. That the lenses always have to be larger than the space provided for their implant in the eye is a principal cause of the trauma.

Implantation of currently used lenses in their proper position within the eye requires the reduction of lens size inside the eye during surgery. In this microfine surgery, the long, thin haptics or feet attached to thin lenses must be manipulated within the eye, often requiring uncommon agility on the part of even skilled surgeons. Space limitations in the eye, the required size of the lens once implanted and considerable manipulations of the lenses during implantation by the surgeon can result in traumatic damage to the corneal endothelium and very often rupture of the posterior capsule by the novice. Damage to the corneal endothelium and rupture of the posterior capsule are complications considered serious.

It would be expedient to offer an intraocular lens, for placement in either the anterior chamber or posterior segment, that could be implanted in a very nearly atraumatic manner.

It would be desirable if an intraocular lens were provided that during surgical implantation was small for easy insertion into the eye with minimum trauma to the cornea and other structures while later being easily made larger to effect a firm, secure fit in the eye. Such lenses could be implanted by relatively inexperienced implant surgeons without considerable manipulations of the lens during surgery. Damage to the corneal endothelium and rupture of the posterior capsule would occur less often, thus minimizing compromises to a patient's welfare.

BRIEF DESCRIPTION OF THE INVENTION

The intraocular lens of this invention is designed for insertion into the anterior chamber or posterior segment of the eye of a mammal. A central lens portion, also referred to as central lenticular means, refracts light that will enter the eye through the cornea before the light passes to the retina. The central lenticular means preferably is made from polymethylmethacrylate. The central lenticular means can be biconvex, convex planar, or convex-concave. Haptic means, feet or loops are attached to the central lenticular portion and function to hold the lens in place in the eye. Haptic means are commonly made from polypropylene.

Generally, the lenses have at least two haptic means, but intraocular lenses with more than two haptic means are not uncommon. First ends of the haptic means are fixed to the central lenticular means. The second end portions of the openable haptic means detachably and resiliently communicate with the central lenticular portion. This arrangement forms what may be referred to as a closed loop structure. The closed loop structure makes the lens design compact, facilitating easy insertion into the eye.

Reducing the size of the entire intraocular lens structure permits generally atraumatic insertion of the lens into the eye obviating extreme surgical manipulations and contortions of the lens within the eye. Once the lens of this invention is inserted into its desired position within the eye, the openable, resilient haptic means easily can be detached permitting expansion of the haptics thus fixing and stabilizing the lens within the eye.

The openable, resilient haptic means on the lenses of the present invention can be attached at their second ends to the central lenticular portion in a variety of ways. Frangible connections can attach the second ends of the openable, resilient haptic means to the central lenticular means. Once these lenses are inserted into the eye, the frangible connections can be broken allowing the resilient haptic means to spring open into place to fix and seat the lens.

An alternative embodiment allows the openable, resilient haptic means to be selectively attachable and detachable with the central lenticular portion. Key means on the ends of the haptic means neatly can fit into elongated channels opening into receiving means forming a key way for receiving the key means on the central lenticular portion. Generally, the key way extends through the lens edge from the lenticular front surface to back surface. That is, the peripheral edge of the central lenticular means is notched clear through. A variety of these structures are possible with the common theme being the key way/key means of attaching the haptic to the central lenticular portion.

In another embodiment, the second ends of the resilient haptic means narrow in diameter. The central lenticular means has a hole therein slightly smaller in diameter than the diameter of the haptic means. One side of the hole is open to a front or back surface of the central lenticular means to form an open channel. The haptic means are press fit into the open-channel hole. Once the lens is implanted, the second end of the haptic means is removed from the open-channel hole permitting expansion of the resilient haptic. Generally, the hole is directed radially into the central lenticular means, but other appropriate directional configurations are possible.

Another embodiment of this invention is an intraocular lens similarly having central lenticular means. Two haptic means of substantially similar length attach at their first ends to the central lenticular portion forming a "figure-eight" configuration. The second ends connect to each other approximately over the middle of the central lenticular means. The haptic means can be connected with a frangible structure. Once the lens is inserted, the frangible structure can be broken to release the resilient haptic means for fixing the lens in place. Alternatively the "figure-eight" configuration of haptic means can be comprised of a single member attached to the central lenticular means at both of its ends. Once this lens is implanted into the eye, the resilient haptic means is broken at a point approximately above the center of the central lenticular portion.

Similarly, the resilient haptic means of the "figure-eight" configuration attach in a key way/key means arrangement. The second end of one haptic comprises the key way and the second end of the other haptic comprises the key which is received in the key way.

A benefit of this invention resides in the ease of insertion and minimal intraocular manipulation offered to the surgeon by the particular designs disclosed herein. The intraocular lens is compact in structure. Trauma associated with insertion and proper placement within the eye thereby is minimized. The possibility of further traumatizing structures of the eye by manipulating unwieldy resilient haptics is eliminated.

Another benefit of this invention is that the use of the intraocular lens is not limited to surgeons having excellent exposure. Relatively inexperienced implant surgeons easily can use the lenses of this invention. Days of training in implanting currently available intraocular lenses can be reduced to only hours of training for implanting the lenses of this invention.

Other benefits and advantages of this invention will become apparent upon reading the following detailed description and appended claims.

BRIEF DESCRIPTION OF THE DRAWINGS

For a more complete understanding of this invention, reference should now be had to the embodiments illustrated in greater detail in the accompanying drawings.

In the drawings:

FIG. 3 is a plan view showing still another intraocular lens of this invention having a "figure-eight" configuration haptic loop.

FIG. 3A is a magnified view of a portion of FIG. 3 showing frangible means on the haptic loop.

FIG. 4 is yet another lens of this invention having a "figure-eight" configuration haptic loop.

FIG. 4A is a magnified view of a portion of FIG. 4 showing haptic means connected by key way/key means.

FIG. 4B is a magnified view of a portion of FIG. 4 showing haptic means openable by severing.

DESCRIPTION OF THE PREFERRED EMBODIMENTS

Figure 1:
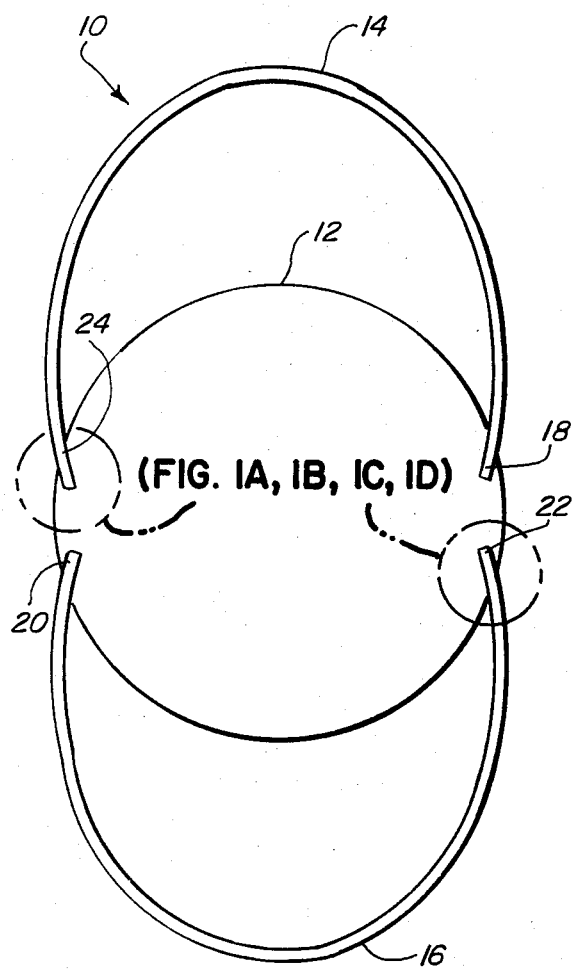
FIG. 1 is a plan view showing an intraocular lens of this invention having two detachable haptic loops.

One embodiment of the intraocular lens 10 of this invention is illustrated in FIG. 1. Intraocular lens 10 has central lenticular means 12 and haptic means 14, 16. Preferably, central lenticular means 12 is made from polymethylmethacrylate, but any material conventionally used is suitable. Resilient haptic means 14, 16 preferably are made from polypropylene, other polyolefin, polymethylmethycrylate, or the like. Resilient haptic means 14, 16 are fixedly attached to central lenticular means 12 at their first ends 18, 20.

Intraocular lens 10 has resilient haptic means 14 and 16 fixedly connected at their first ends 18, 20 and diagonally opposed. That is, a line connecting the fixed first ends 18, 20 will pass through or near the center of central lenticular means 12. Similarly, detachable second ends 22, 24 are diagonally opposed.

Central lenticular means 12 can be a bi-convex, convex planar, or convex-concave lens power typically used in conventionally available intraocular lenses. Also, fixed first end 18, 20 can be fixed to central lenticular means 12 using currently available techniques.

FIGS. 1A through 1D illustrate alternative embodiments of detachably communicating haptic means 14, 16 at their second ends 22, 24 to central lenticular means 12. Except as hereinafter noted, central lenticular means 12 is substantially similar to central lenticular means 12a, 12b, 12c and 12d. It should be appreciated that second ends 22, 24 of haptic means 14, 16 can detachably communicate with central lenticular means 12 using the same manner of detachable structure or different combinations of the detachable structures shown. In the interest of clarity, reference numerals refer only to haptic means 16 and second end 22.

Haptic means 16a terminates at its second end 22a in key means 26. Key means 26 is received by key way 28 in central lenticular means 12a. Key way 28 compromises channel means 30 and receiving means 32. Haptic means 16a generally is at an angle to the horizontal plane of central lenticular means 12a which urges key means 26 into locked position within key way 28. Minor manipulations by a skilled surgeon, once the lens is implanted, will release resilient haptic means 16a, unlocking key means 26 from key way 28 causing haptic means 16a to spring open.

Figure 1A:
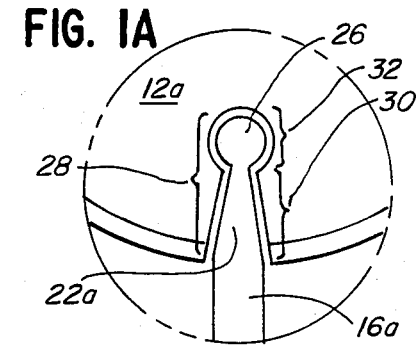
FIG. 1A is a magnified view of a portion of FIG. 1 showing the detachable haptic end communicating with the central lenticular portion with a key way/key means.
Figure 1B:
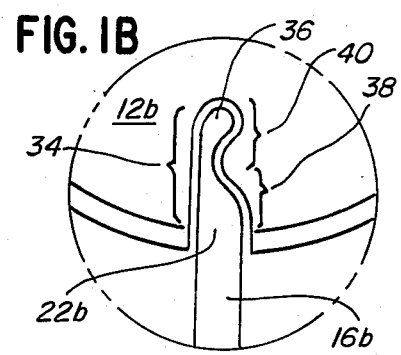
FIG. 1B is a magnified view of a portion of FIG. 1 showing the detachable haptic end communicating with the central lenticular portion with another key way/key means embodiment.

Resilient haptic means 16b fits neatly into key way means 34 in central lenticular means 12b as illustrated in FIG. 1B. Second end 22b of resilient haptic means 16b terminates in key means 36. Key way means 34 is comprised of elongated channel means 38 opening into receiving means 40 for receiving key means 36.

Resilient haptic means 16b lies generally in the horizontal plane of central lenticular means 12b. Key means 36 thus is locked in receiving means 40. Once implanted, an intraocular lens having resilient haptic means 16b with key means 36 may be unlocked and sprung open by exerting a small force on resilient haptic means 16b perpendicular to the horizontal plane of central lenticular means 12b. This force urges key means 36 of resilient haptic means 16b out of key way means 34.

Figure 1C:
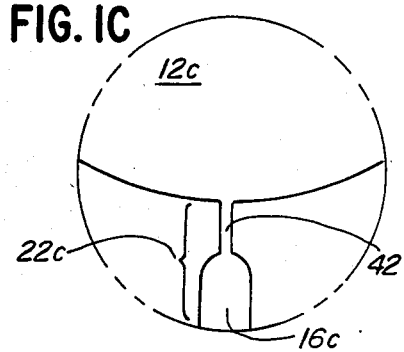
FIG. 1C is a magnified view of a portion of FIG. 1 showing the detachable haptic end communicating with the central lenticular portion with frangible means.

FIG. 1C shows resilient haptic means 16c having second end 22c connected to central lenticular means 12c via frangible means 42. An implanted intraocular lens having resilient haptic means 16c and frangible means 42 requires a surgeon to break frangible means 42 to spring open resilient haptic means 16c thereby seating the intraocular lens in a mammalian eye.

Figure 1D:
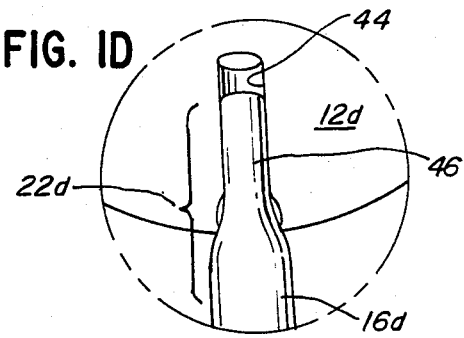
FIG. 1D is a magnified view of a portion of FIG. 1 showing the detachable haptic end press-fit communicating with the central lenticular portion.

Second end 22d of resilient haptic means 16d is illustrated in FIG. 1D. Central lenticular means 12d has open-channel hole 44 therein. Open-channel hole 44 is open to a front or back surface of the central lenticular means 12d to form an elongated open channel. Open-channel hole 44 preferably is inwardly, radially directed, but other appropriate directional configurations of hole 44 are possible. Resilient haptic means 16d, terminating in press-fit end 46 is press fit into hole 44 which preferably is of smaller diameter than press-fit end 46. Resilient haptic means 16d is sprung open once the intraocular lens on which it resides is implanted. Resilient haptic means 16d is pulled up and away from open-channel hole 44 to spring it open.

Generally, resilient haptic means 16a, 16b, and 16d are selectively detachable from and attachable to their respective central lenticular means. Resilient haptic means 16c generally is intended for one time detaching.

Figure 2:
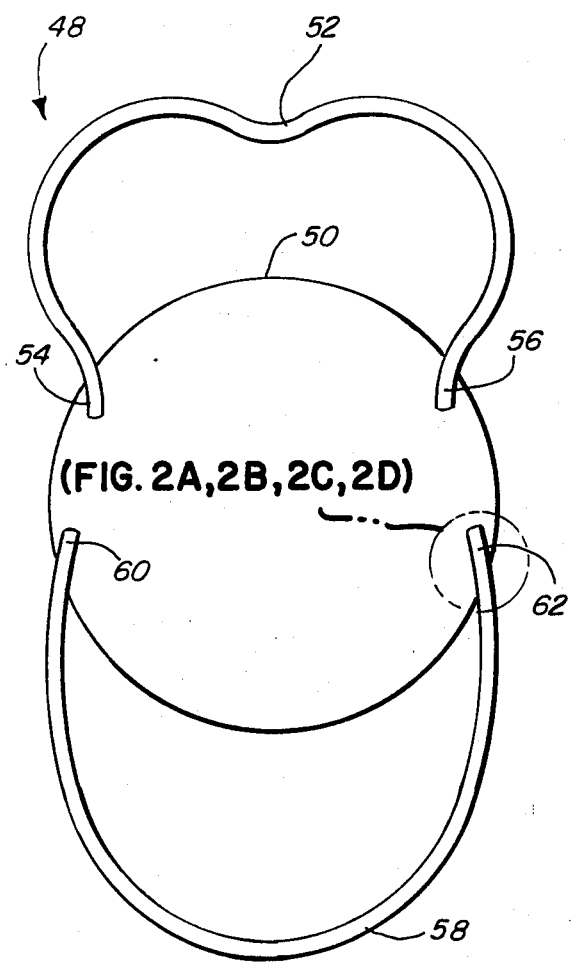
FIG. 2 is a plan view showing an intraocular lens of this invention having one detachable haptic loop and one fixed-end haptic loop.

Intraocular lens 48 is shown in FIG. 2. Central lenticular means 50 has haptic means 52 fixed to it by using currently known techniques at first end 54 and second end 56 of haptic means 52. Haptic means 52 is in a fixed, closed configuration. Resilient haptic means 58 is fixed at first end 60 to central lenticular means 50 using currently known techniques. Second end 62 communicates with central lenticular means 50 as shown in the magnified views of FIGS. 2A through 2D. The detachable haptic embodiments illustrated in FIGS. 2A through 2D function identically to the haptic embodiments shown in FIGS. 1A through 1D.

Resilient haptic means 58a terminates in second end 62a having key means 64. Key means 64 is received in receiving means 66 of key way means 68. Resilient haptic means 58b terminates in second end 62b having key means 70. Central lenticular means 50b has key way means 72. Resilient haptic means 58c terminates in second end 62c having frangible means 74 communicating with central lenticular means 50c. Second end 62d of resilient haptic means 58d has press-fit end 76 received in open-channel hole 78.

FIGS. 3 and 4 represent "figure-eight" embodiments of the intraocular lens of this invention. Intraocular lens 80 has central lenticular means 82. Resilient haptic means 84, 86 are fixed at their first ends 88, 90 to central lenticular means 82 by conventional techniques. First ends 88, 90 are fixed to central lenticular means 82 diagonally opposed to each other. Resilient haptic means 84, 86 are detachably connected by frangible means 92 at second ends 85, 87 to form a "figure-eight" configuration. Frangible means 92 is located approximately near the center of central lenticular means 82. When frangible means 92 is broken, resilient haptic means 84, 86 spring open to seat implanted intraocular lens 80 in a mammalian eye.

Intraocular lens 80a in FIG. 4 is substantially similar to intraocular lens 80 except as hereinafter noted. FIG. 4B illustrates that resilient haptic means 84b can comprise one haptic means with first end 88a and second end 90a fixedly attached using conventional techniques to central lenticular means 82a. Resilient haptic means 84a can be severed approximately at the center of central lenticular means 82a causing resilient haptic means 84a to spring open thereby seating implanted intraocular lens 82a in an eye. Two haptic means roughly of similar length are formed.

Figure 2A:
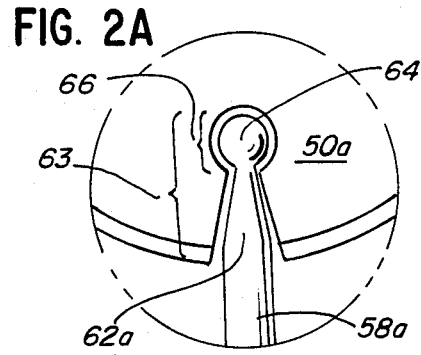
FIG. 2A is a magnified view of a portion of FIG. 2 showing the detachable haptic end communicating with the central lenticular portion with a key way/key means.
Figure 2B:
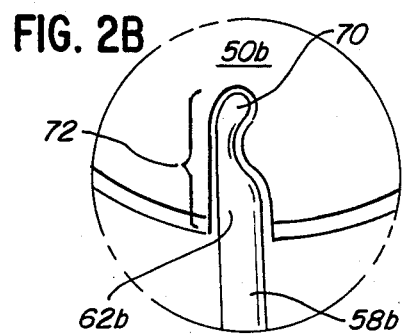
FIG. 2B is a magnified view of a portion of FIG. 2 showing the detachable haptic end communicating with the central lenticular portion with another key way/key means embodiment.
Figure 2C:
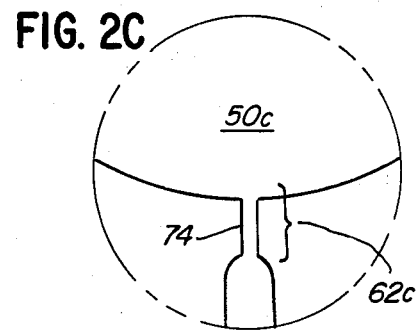
FIG. 2C is a magnified view of a portion of FIG. 2 showing the detachable haptic end communicating with the central lenticular portion with frangible means.
Figure 2D:
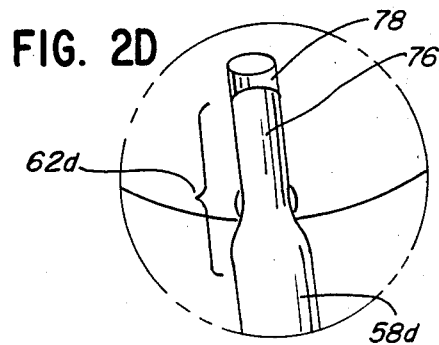
FIG. 2D is a magnified view of a portion of FIG. 2 showing the detachable haptic end press-fit communicating with the central lenticular portion.

Alternatively, second ends 85a, 87a of resilient haptic means 84a, 86a, can form a key way/key structure similar to the structures of FIGS. 1A and 2A described above. Second end 87a terminates in key means 94. Second end 85a terminates in key way means 96 comprised of elongated channel 98 opening into receiving means 100. Resilient haptic means 84a, 86a are sprung open by dislodging key means 94 from receiving means 100 of key way means 96.

It should be appreciated that the embodiments of this invention described above result in a compact intraocular lens structure which is easily implantable. Trauma generally associated with implantation of intraocular lenses can be reduced by use of this invention, and relatively inexperienced implant surgeons easily can use the lenses of this invention.

The above has been offered for illustrative purposes and is not intended to limit the invention of this application which is defined in the claims below.

I claim:

1. Intraocular lens for insertion inside the eye of a mammal comprising:

central lenticular means for refracting light entering the eye through the cornea before the light passes to the retina; and, at least two resilient haptic means for stabilizing and holding in place in the eye said central lenticular means, first ends of said resilient haptic means fixedly attached to said central lenticular means and second ends of said resilient haptic means wherein one of said second ends of said resilient haptic means terminates in key means for selectively attaching and detaching one of said second ends to another of said second ends defining elongated channel means opening into receiving means for receiving said key means.

2. Intraocular lens for insertion inside the eye of a mammal comprising:

central lenticular means for refracting light entering the eye through the cornea before the light passes to the retina; and, resilient haptic means for stabilizing and holding in place in the eye said central lenticular means having first and second ends of said resilient haptic means fixedly attached to said central lenticular means and generally forming a "figure-eight" configuration over said central lenticular means whereby said resilient haptic means can be severed generally over the center of said central lenticular means.

* * * * *